United States Patent
Jonjic

[11] Patent Number: 5,984,676
[45] Date of Patent: *Nov. 16, 1999

[54] PALATAL PLATE PROSTHESIS PRODUCTION FASTENER

[76] Inventor: Leo Jonjic, IKA 31 c. M. Tita, Tita, Croatia

[*] Notice: This patent is subject to a terminal disclaimer.

[21] Appl. No.: 09/050,236

[22] Filed: Aug. 3, 1998

Related U.S. Application Data

[63] Continuation of application No. 08/562,378, Nov. 24, 1995.

[30] Foreign Application Priority Data

May 6, 1995 [HR] Croatia .................................. P950318

[51] Int. Cl.[6] ........................................................ A61C 3/00
[52] U.S. Cl. ................................................ 433/50; 433/56
[58] Field of Search ................................... 433/50, 56, 75

[56] References Cited

U.S. PATENT DOCUMENTS

| | | | |
|---|---|---|---|
| 1,753,965 | 4/1930 | Ralph | 433/56 |
| 2,724,899 | 11/1955 | Stoll | 433/75 |
| 3,760,504 | 9/1973 | Ljubarsky et al. | 433/50 |
| 4,501,556 | 2/1985 | Zelnigher | 433/56 |
| 4,762,490 | 8/1988 | Ludwigs | 433/56 |
| 5,257,932 | 11/1993 | Leinfelder et al. | 433/56 |

*Primary Examiner*—John J. Wilson

[57] ABSTRACT

The instant invention provides a novel apparatus; a novel method of using the apparatus; and a novel prosthesis made by the method of using the apparatus. The invention provides an apparatus for forming a palatal plate prosthesis of a substantially precise, predetermined uniform thickness, comprising: a frame; a first component further including elements for enabling it to be detachably fixed to each of the first support, the second support and the third support for detachably fixing a first casting to the frame; and pivotally attached to the first support and the second support for enabling a second casting to be pivoted relative to the first casting; wherein the elements are designed for causing the first casting to generally lie in a first horizontal plane when the first component is detachably fixed to the support; and, a second component attached to the upper portion of the frame generally spaced from and parallel to each the support, for movably fixing a second casting to the frame, sufficient for enabling the second casting to lie generally in a second plane which is generally parallel to, and equidistant from, the first horizontal plane when the first component is detachably fixed to the support.

11 Claims, 10 Drawing Sheets

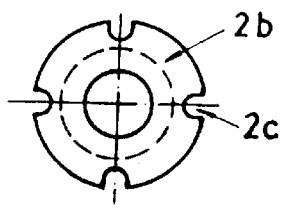
FIG. 3 A
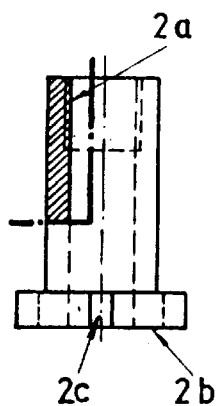
FIG. 3 B
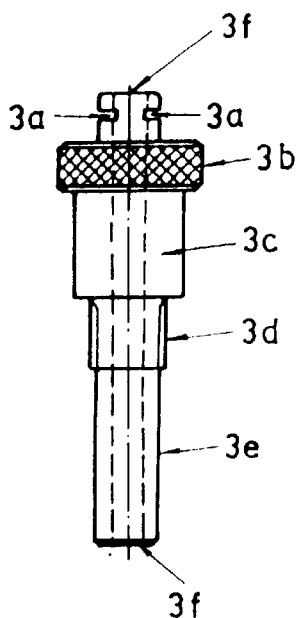
FIG. 4 A
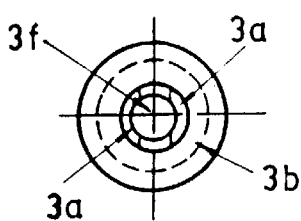
FIG. 4 B
FIG. 5 A
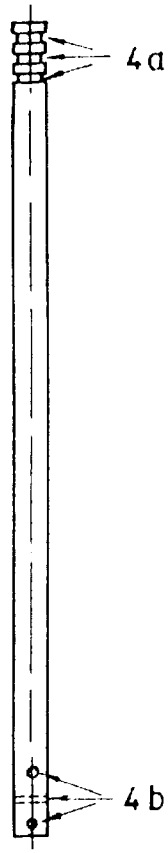
FIG. 5 B
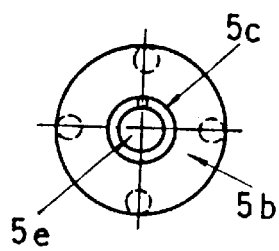
FIG. 7 A
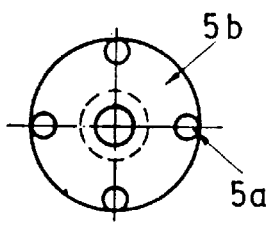
FIG. 7B
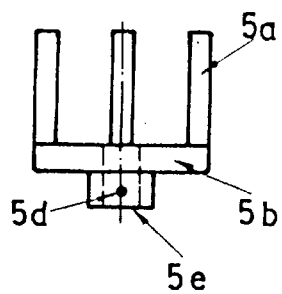
FIG. 7 C
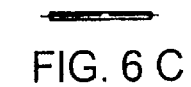
FIG. 6 A
FIG. 6 B
FIG. 6 C

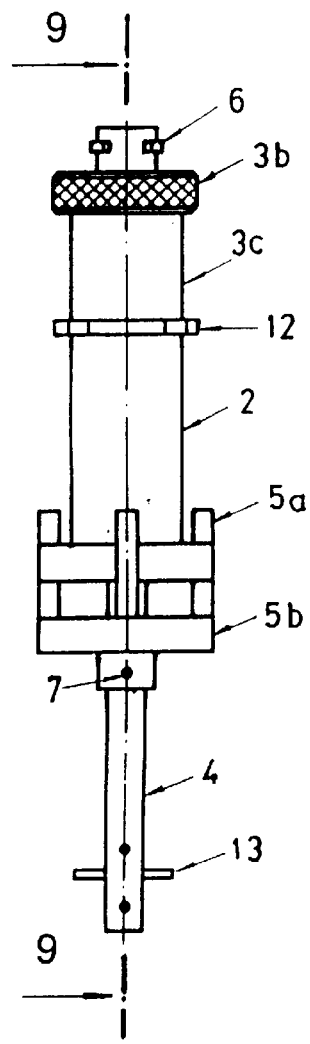
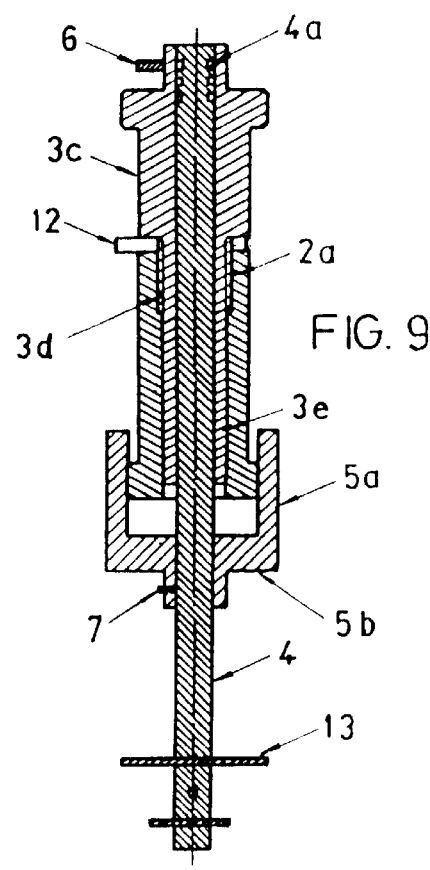

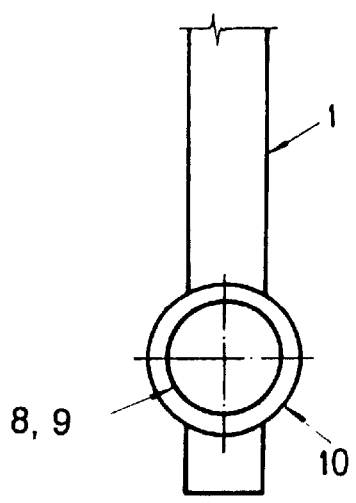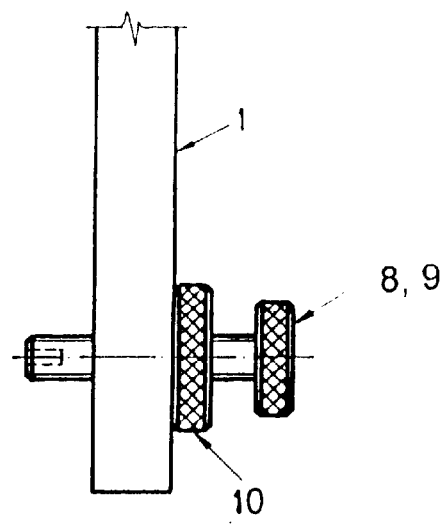
FIG. 13 A  FIG. 13 B

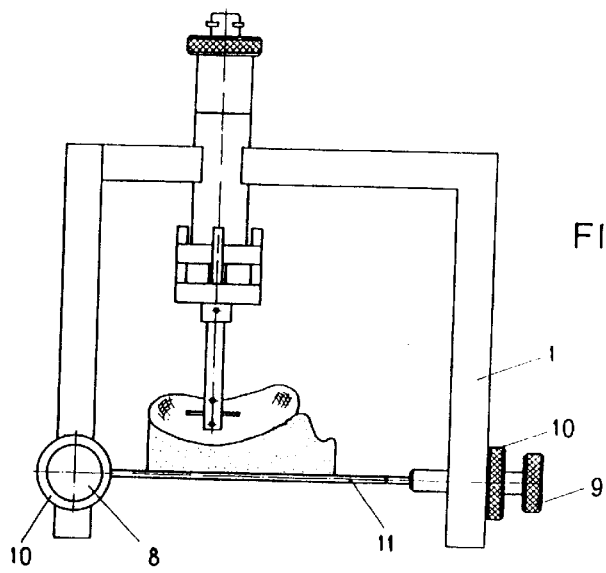
FIG. 16
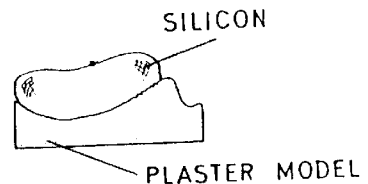
FIG. 14
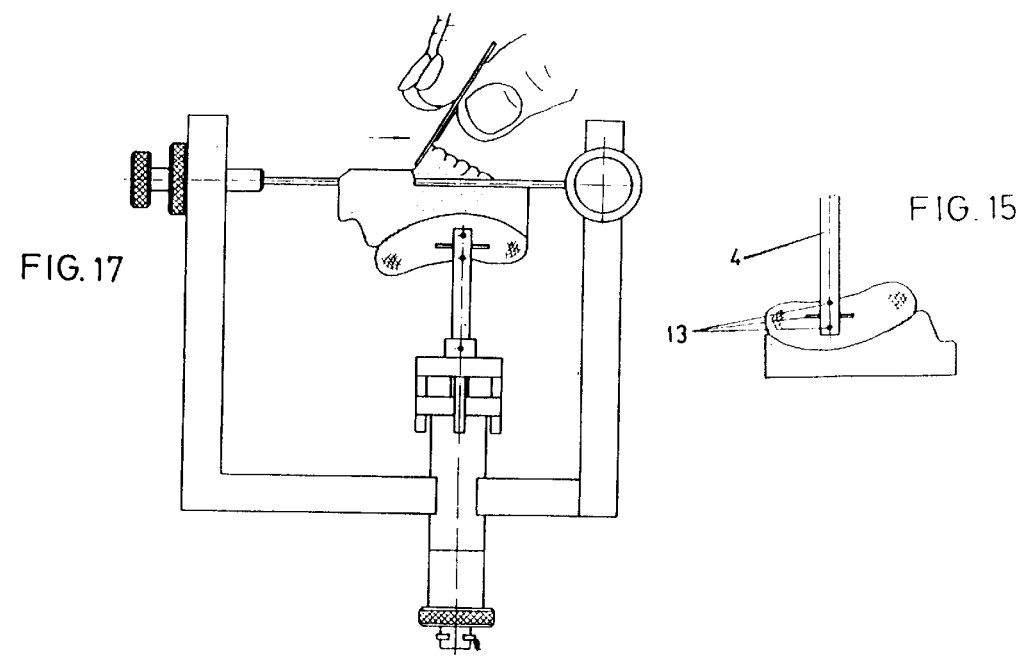
FIG. 17
FIG. 15

PALATAL PLATE PROSTHESIS PRODUCTION FASTENER

RELATED APPLICATION DATA

This is a continuation of application Ser. No. 08/562,378 filed Nov. 24, 1995.

BACKGROUND OF THE INVENTION

The instant invention broadly relates to the field of medical instruments and methods of their use. More specifically, the invention relates to dental laboratory equipment and methods of their use. Still more specifically, the invention relates to an apparatus for the production of a palatal plate prosthesis and a method of its use.

One way of rehabilitating a dental patient's gnathic system is by fashioning either a partial or complete palatal prosthesis. Although, the process comprises conventional steps, it nonetheless must typically be customized to some extent in order to accommodate the needs of the individual patient.

The palatal prosthesis comprises a convexity relief and a concave relief. The convexity relief is that part of the prosthesis which contacts the patient's palate, and thus, must conform to all contours of it. The concave relief is that part of the prosthesis which contacts the patient's tongue when in use. Prior to the instant invention, the uniformity and the thickness of a prosthesis was a matter defined by the skill of the particular dental technician. The uniformity and thickness of a newly fashioned palatal prosthesis are important factors relative to the patient's adaptation to it. Non-uniformity and improper thickness of a prothesis often cause phonetic flaws in the speech of the patient wearing it. These phonetic flaws often manifest themselves in the form of an uncontrollable "hissing." It has been speculated that this "hissing" phenomenon results when air circulates between the tongue and the smooth part of an improperly fashioned prosthesis.

Since the are typically relatively massive and non-uniformly thick, conventional "ready-made" prostheses, at best, offer only inconsistent success to the solution of the "hissing phenomenon." Typically, a substantial period of time is required for a patient to become accustomed to such a prosthesis. Even custom fashioning by a skilled dental technician cannot insure that improper and non-uniform thickness of the prosthesis will nonetheless cause "hissing." Thus, there exists a long felt need for an effective solution to the "hissing phenomenon."

SUMMARY OF THE INVENTION

The instant invention in large part solves the problems of the prior and fulfills this long felt need.

Mores specifically, it is an object of the invention to provide an apparatus a method for using the apparatus for satisfying this long felt need.

Still more specifically, it is an object of the invention to provide an apparatus a method for using the apparatus for enabling the formation of a palatal prosthesis having a uniformly minor thickness.

Still even more specifically, it is an object of the invention to provide an apparatus a method for using the apparatus for enabling the formation of a palatal prosthesis having a thickness sufficiently uniform and sufficiently thin so as to avoid the "hissing phenomenon," and reduce the time period which would otherwise be required for the patient to become accustomed to the prosthesis.

BRIEF DESCRIPTION OF THE DRAWINGS

FIG. 3 shows side elevation and bottom plan partial views of the cylinder element of the invention.

FIG. 4 shows side elevation and bottom plan partial views of the shaft elevator element of the invention.

FIG. 5 shows a side elevation partial view of the elevator element of the invention.

FIG. 6 shows elevation side and end partial views of the lower casting retention elements of the invention.

FIG. 7 shows elevation side top plan and bottom plan partial views of the shaft crown element of the invention.

FIG. 8 shows a side elevation view of the shaft and shaft elevator assembly of the invention.

FIG. 9 shows a side elevation view of the shaft and shaft elevator assembly of the invention, rotated 90° about its longitudinal axis relative to FIG. 8.

FIG. 13 shows side elevation and plan partial views of the mounted lower casting mounting element retention pivoting bolt assembly.

FIG. 14 shows side elevation cutaway partial view of the conventional formation of the lower casting using a temporary silicone impression of the patient's palate, before the lower casting is mounted on the lower casting mounting element of the invention.

FIG. 15 shows a side elevation cutaway partial view of FIG. 14 the lower casting before mounting on the lower casting mounting element, but after mounting of the temporary silicone impression on the shaft of the invention.

FIG. 16 shows a side elevation view of the entire apparatus of the invention further showing the lower casting before mounting on the lower casting mounting element, but after the temporary silicone impression is mounted on the shaft elevator/shaft assembly of the invention.

FIG. 17 shows a side elevation view of the entire apparatus of the invention inverted to enable the lower casting to be mounted on the lower casting mounting element, after the temporary silicone impression is mounted on the shaft elevator/shaft assembly of the invention.

DETAILED DESCRIPTION OF TEE INVENTION

As noted above, FIG. 1 shows an isometric view of the apparatus of the instant invention in its entirety, depicting all its elements. The basic elements of the apparatus are: frame 1, shaft/shaft elevator assembly 2–5, 12 and 13; lower casting mounting assembly 8–11. Frame 1 includes a portion having a "T" shaped plan view; and, a lower portion including Three (3) posts. Each posts includes a bore therethrough for fixing One (1) extremity of the lower casting mounting element of FIG. 11, to a respective post of frame 1.

Figure 2:
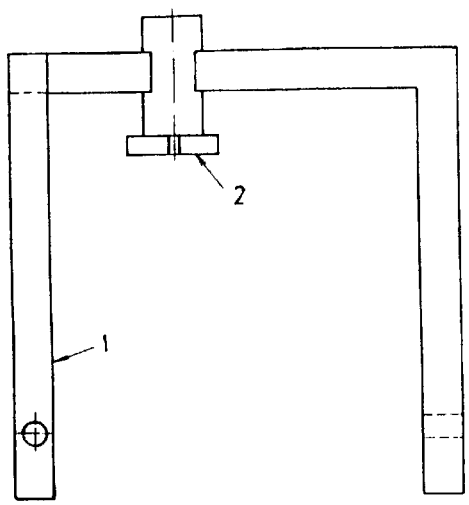
FIG. 2 shows a front elevation, side elevation (without shaft elevator and shaft) and plan partial view of the apparatus of the invention.
Figure 2:
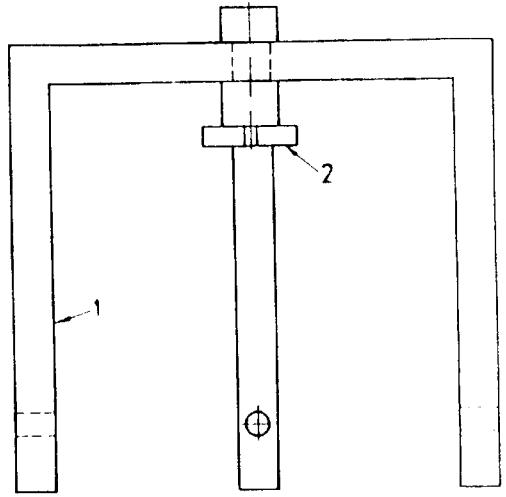
Figure 2:
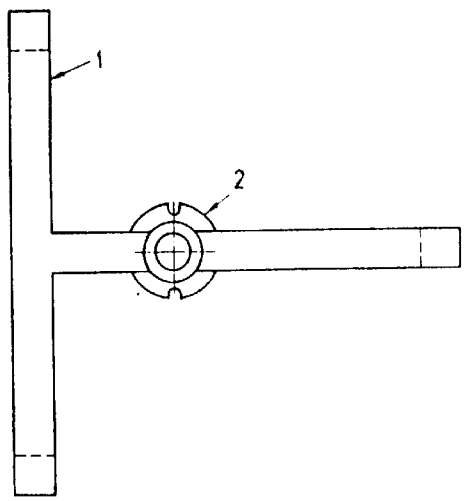

As noted above, FIG. 2 shows a front elevation, side elevation (without shaft elevator and shaft) and plan partial views of the apparatus of the invention. Depicted, is the manner in which the the shaft/shaft elevator assembly (illustrated in the figure by only its cylinder element 2) is mounted on the frame 1.

As noted above, FIG. 3 shows side elevation and bottom plan partial details of the cylinder element 2. Specifically depicted is the center bore through cylinder 2, which comprises an upper inner screw threaded portion 2a and a base 2b further including notches 2c.

FIG. 4 shows side elevation and bottom plan partial details of the shaft elevator element. Specifically depicted are: shaft elevator 3 which includes central bore 3f for accommodating shaft 4; middle screw threaded portion 3d for engaging the upper inner screw threaded portion 2a of cylinder 2; smooth lower portion 3e; knurled portion 3b for facilitating finger turning of shaft elevator 2 when mounted in frame 1; and, side grooves 3a for enabling support of shaft 4 by shaft elevator 2 and shaft safety retainer 6.

FIG. 5 shows a side elevation partial view of the shaft element. Also depicted are circumferential grooves 4a for engaging shaft safety retainer 6 and radial bores 4b for enabling shaft 4 to be vertically supported by shaft elevator 2 though shaft safety retainer 6.

FIG. 6 shows elevation side and end partial views of the lower casting retention elements 13.

FIG. 7 shows elevation side top plan and bottom plan partial views of the shaft crown element. More particularly depicted are shaft crown base 5b, shaft crown posts 5a for the accommodating notches 2c and for providing force fitted engagement with cylinder base 2b; and, the crown post collar at the base of shaft crown base 5b, which includes central bore 5e for accommodating shaft 4, a set screw, and set screw bore 5d, for substantially fixing shaft 4 to shaft crown 5.

FIG. 8 shows a side elevation view of the shaft and shaft elevator assembly. The shaft elevator assembly, includes: shaft elevator 3, further including middle screw portion 2d; knurled shaft elevator rotating collar 3b; shaft 4; shaft crown 5, including shaft crown posts 5a; and, cylinder 2, including cylinder base 5b, further including notches 2c for force fit fixing cylinder base 5b against shaft crown posts 5a.

FIG. 9 shows a cutaway partial elevation view of the shaft elevator assembly, rotated 90° about its longitudinal axis, relative to FIG. 8. Shaft elevator 3 includes knurled collar 3b; outer screw threads 2a at its outer mid portion; and, shaft safety retainer 6 for vertically fixing shaft 4 to shaft elevator 3. It is the only element depicted in FIG. 9 which is designed to be rotated about the central longitudinal axis of the assembly. All other elements depicted in FIG. 9 are not rotatable about the longitudinal axis of the assembly. The figure also depicts shaft 4, which includes at the lowest, end thereof upper casting retention elements 13. Further shown is shaft crown 5 which includes shaft crown base 5b and shaft crown posts 5a. Shaft crown 5 is fixed to shaft 4 by a set screw generally shown at 7. Still further shown is cylinder 2 which includes a screw threaded inner surface 2a at its upper most end, for engaging the screw threads 3d of shaft elevator 3; and cylinder base 2b, which includes notches 2c for engaging crown posts 5a in a force fit relationship sufficient to substantially fix cylinder 2 to shaft crown 5.

Figure 10:
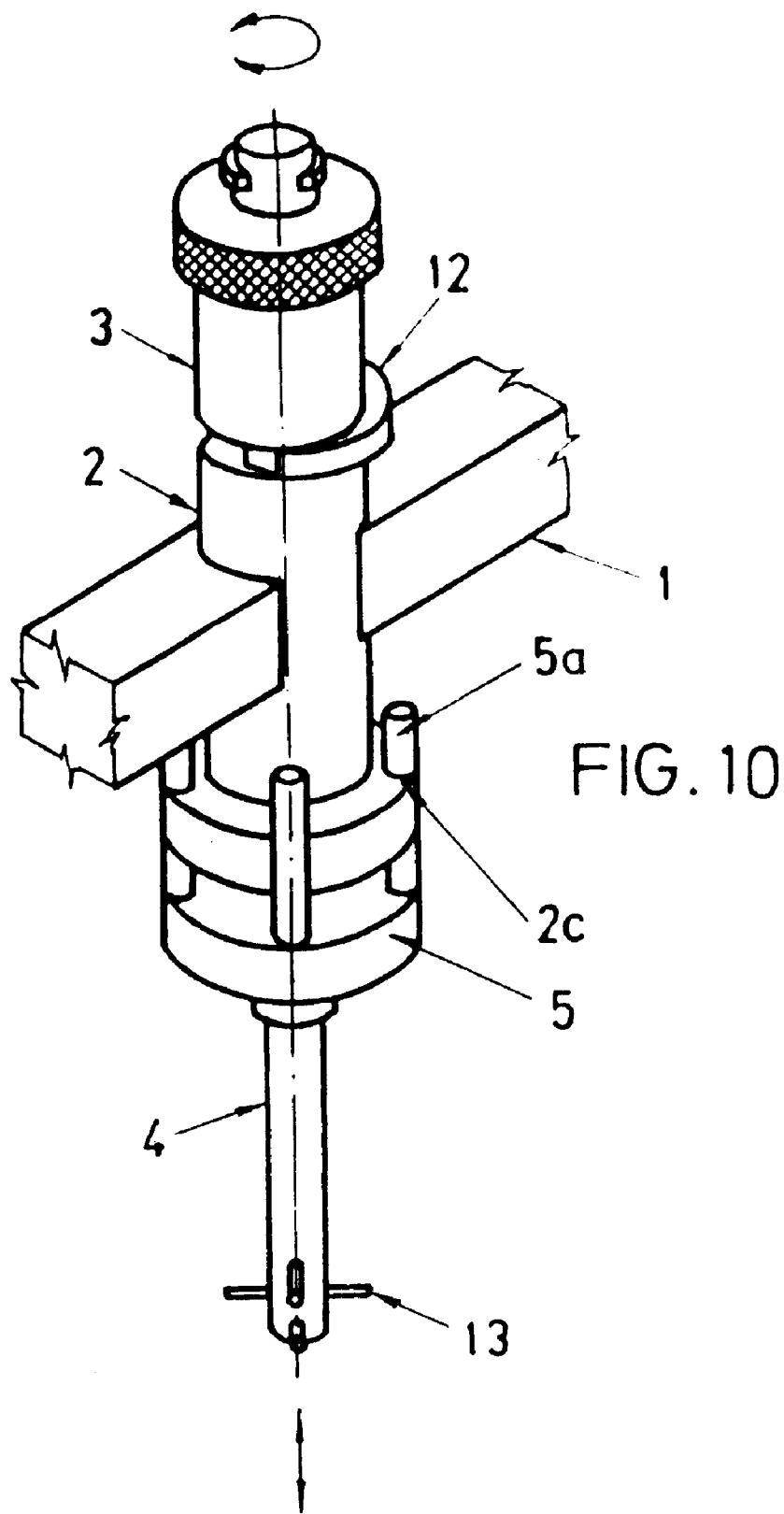
FIG. 10 shows an isometric partial view of the mounted shaft and shaft elevator assembly of the invention.

FIG. 10 shows an isometric partial view of the mounted shaft and shaft elevator assembly. Depicted are: a fragmentary portion of frame 1 for supporting the shaft/shaft elevator assembly; shaft elevator 3; cylinder 2 and cylinder notches 2c; shaft crown 5 and shaft crown posts 5a; and, shaft 4 with upper casting retention elements 13.

Figure 11:
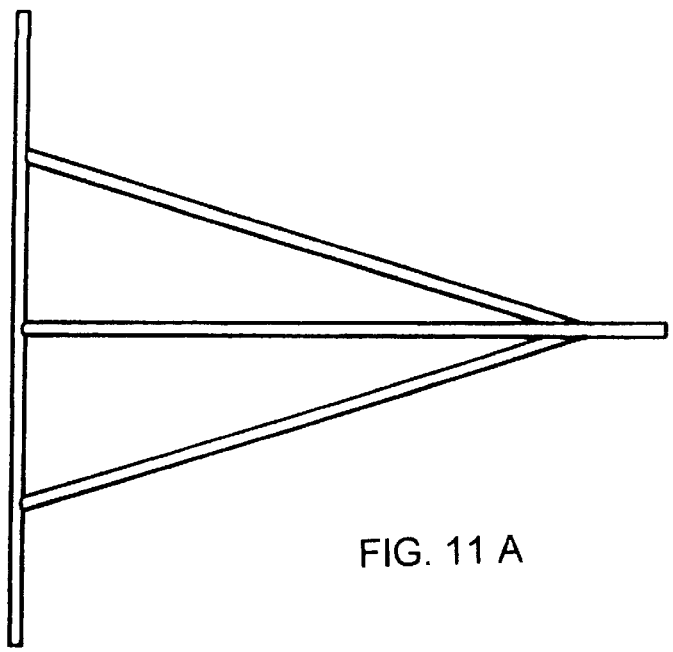
FIG. 11 shows side elevation and plan partial views of the lower casting mounting element of the invention.
Figure 11:

FIG. 11 shows side elevation and plan partial views of the lower casting mounting element 11 comprised of a "T" shaped member and Two (2) support members for supporting the head of the "T" member (as opposed to the head support member of the "T"). Not particularly depicted is the screw threading at the Three (3) exposed ends of the "T" head and "T" support.

Figure 1:
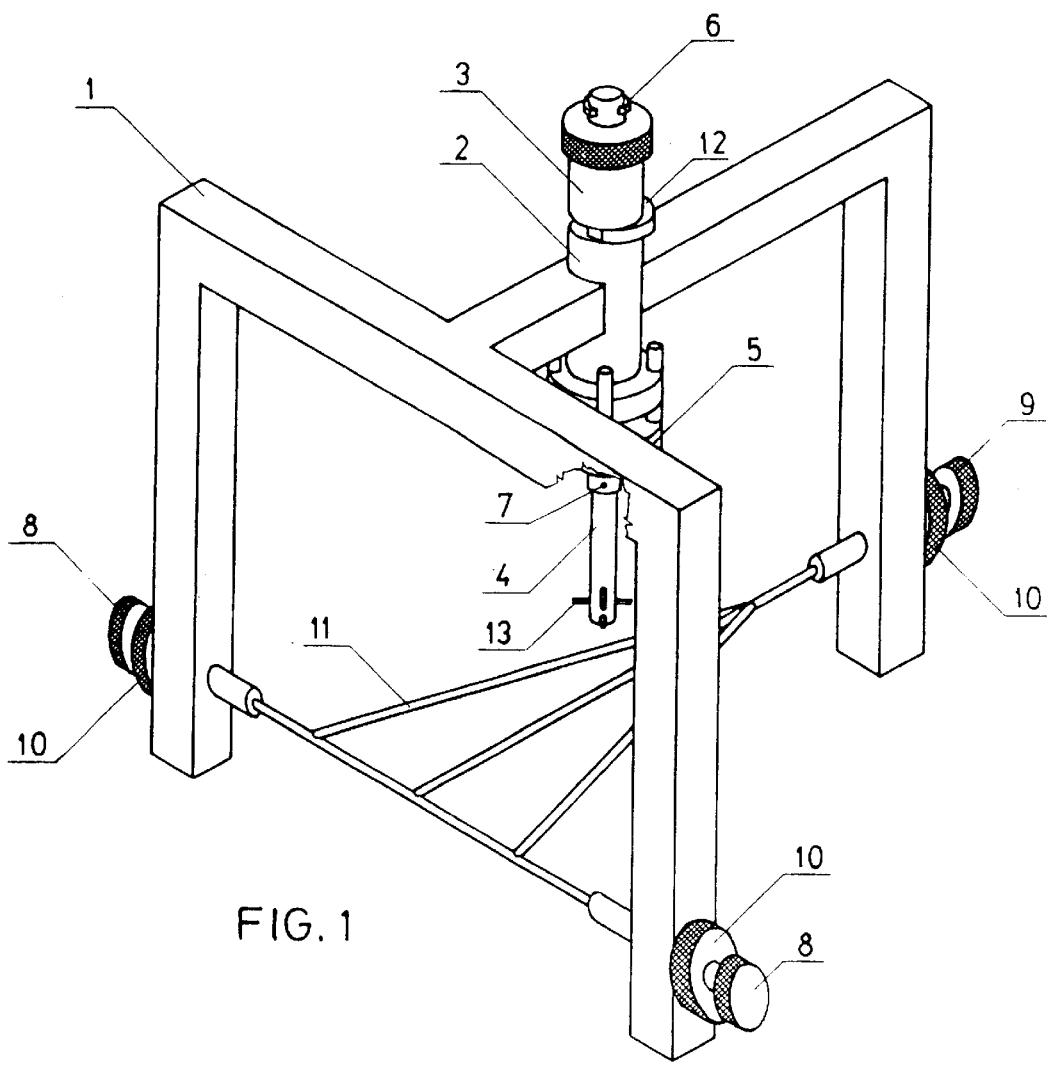
FIG. 1 shows an isometric view of the apparatus of the instant invention in its entirety, depicting all of its elements.
Figure 12:
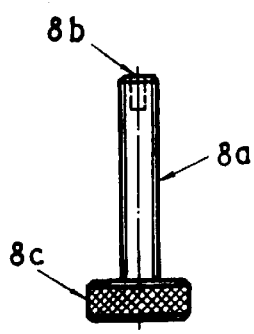
FIG. 12 shows side elevation and plan partial views of the lower casting mounting element retention bolt assembly.
Figure 12:
Figure 12:
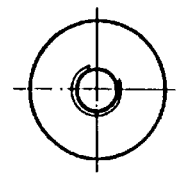
Figure 12:

FIG. 12 shows side elevation and plan partial views of the lower casting mounting element retention bolt assemblies for detachably fixing each of the exposed ends of the lower casting mounting element 11 to frame 1. Each assembly comprises an outer screw threaded rod member 8a perpendicularly attached to a disk-like base 8c and an outer knurled nut 10 for engaging the outer screw threads of rod member 8a when the lower casting mounting element is fixed in frame 1 as shown in FIG. 1. The end of the rod opposite the disk, farther comprises axial threaded bore 8b (shown in a phantom view), for accommodating a screw threaded exposed end of the lower casting mounting element 11 when the apparatus is being manipulated as depicted in FIG. 1.

FIG. 13 shows side elevation and plan partial views of the mounted lower casting mounting element retention pivoting bolt assembly. Depicted specifically in relationship to a fragmentary front and side elevation views of frame 1, are the elements shown in FIG. 12, including: threaded rod member 8a; knurled nut 10; a phantom view of 8b; and, knurled disk-like base 8, 9.

FIG. 14 shows side elevation cutaway partial view of the conventional formation of the lower casting using a temporary silicone impression of the patient's palate, before the lower casting is mounted on the lower casting mounting element.

FIG. 15 shows a side elevation cutaway partial view of FIG. 14 of the lower casting before mounting on the lower casting mounting element, but after mounting of the temporary silicone impression on the shaft 4 with upper casting retention elements 13.

FIG. 16 shows a side elevation view of the entire apparatus further showing the lower casting before mounting on the lower casting mounting element, but after the temporary silicone impression is mounted on the shaft elevator/shaft assembly. Shaft 4 is lowered to its lowest position against lower casting support 11, prior to fixing it to the lower casting support 11. Specifically depicted are threaded rod member(s) 8a; knurled nut(s) 10; and, knurled disk-like base(s) 8, 9.

FIG. 17 shows a side elevation view of the entire apparatus inverted to enable the lower casting to being mounted on the lower casting mounting element, after the temporary silicone impression is mounted on the shaft elevator/shaft assembly. After the apparatus is inverted, a layer of plaster or other suitable fixing material is applied to the bottom of the lower casting; and, between and around the members of the lower casting support sufficient to fix to the lower casting support.

Figure 18:
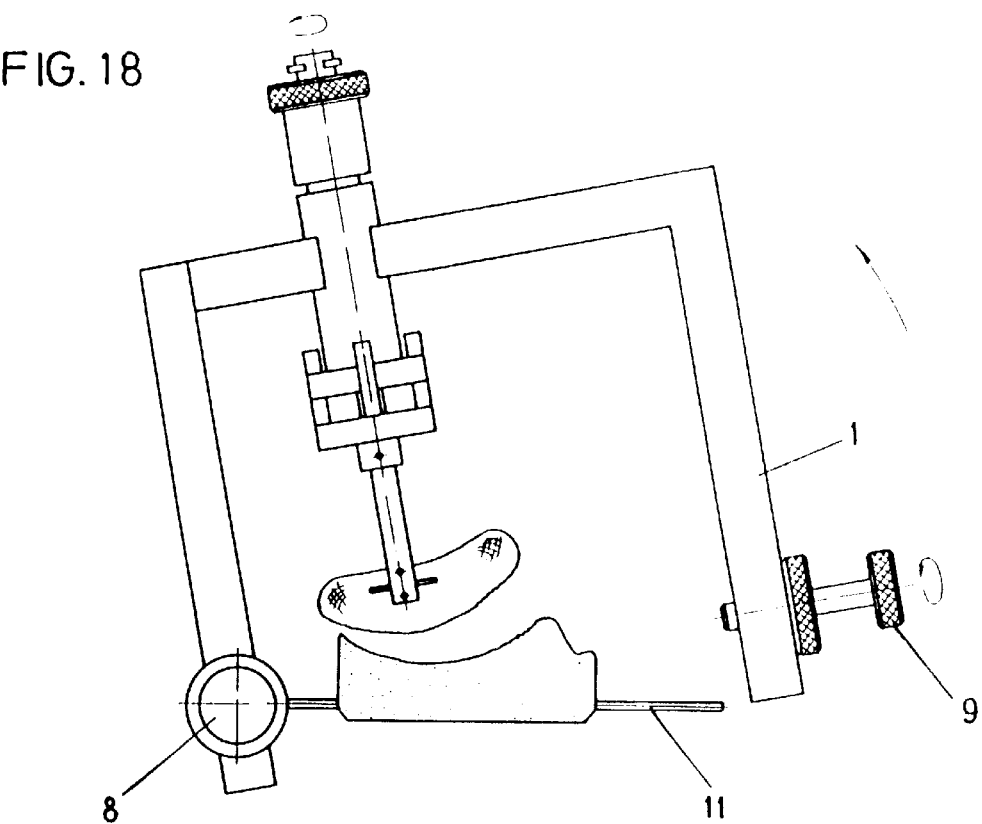
FIG. 18 shows a side elevation view of the entire apparatus of the invention after the lower casting mounting element is detached from the frame of the apparatus and the frame is pivoted about the lower casting mounting element retention pivotal bolt assembly to enable separation of the temporary silicone impression from the lower casting.

FIG. 18 shows a side elevation view of the entire apparatus after the lower casting mounting element is detached from the frame of the apparatus and the frame is pivoted about the lower casting mounting element retention pivotal bolt assemblies to enable separation of the silicone impression from the lower casting. The "T" head support portion of the lower casting support 11 is unscrewed from the post of frame 1 which supported it, and frame 1 is pivoted about the two remaining unscrewed lower casting mounting element retention bolt assemblies 8–10 sufficient to separate the temporary silicone impression from the lower casting.

Figure 19:
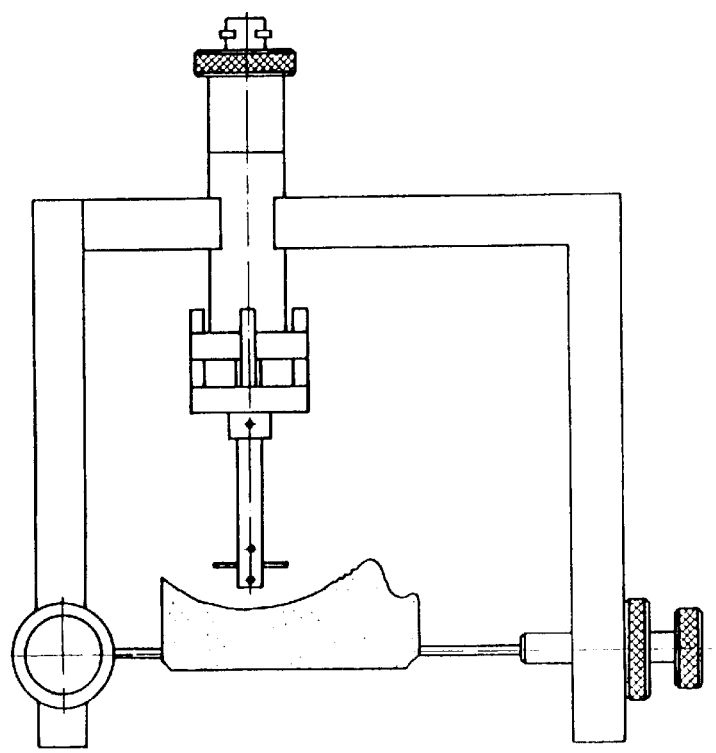
FIG. 19 shows a side elevation view of the entire apparatus of the invention after temporary silicone impression has been removed from the shaft of the invention and the lower casting mounting element had been reattached to the frame of the apparatus.
Figure 20:
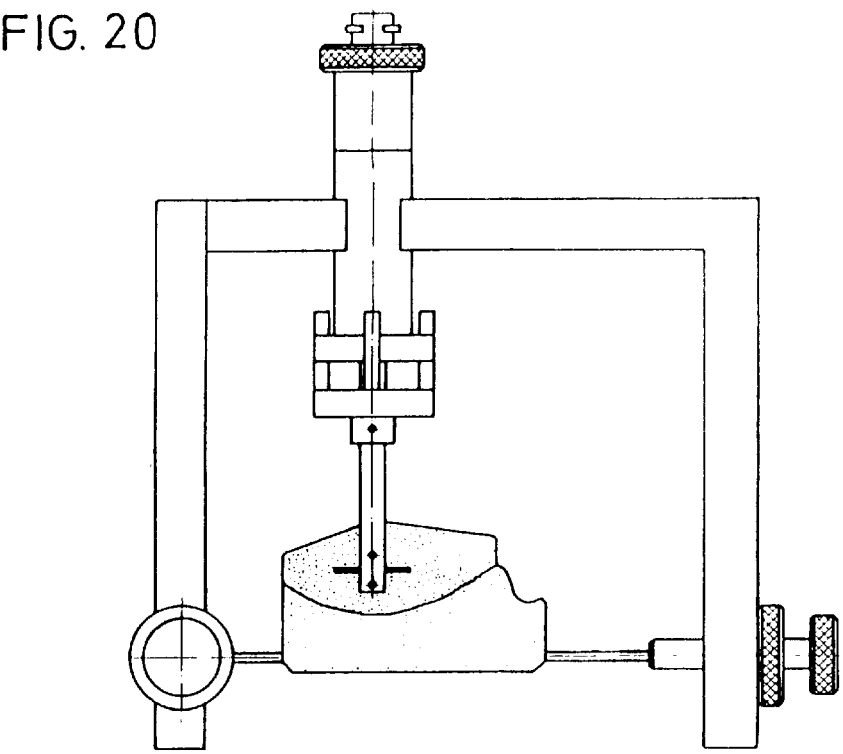
FIG. 20 shows a side elevation view of the entire apparatus of FIG. 19 after the permanent upper casting has been formed on the lower casting by conventional methods.

FIG. 19 shows a side elevation view of the entire apparatus after temporary silicone impression has been removed from the shaft and the lower casting mounting element had been reattached to the frame of the apparatus, prior to the formation of the permanent upper casting as more particularly described in FIG. 20.

FIG. 20 shows a side elevation view of the entire apparatus of FIG. 19 after the permanent upper casting has been formed on the lower casting by conventional methods.

Figure 21:
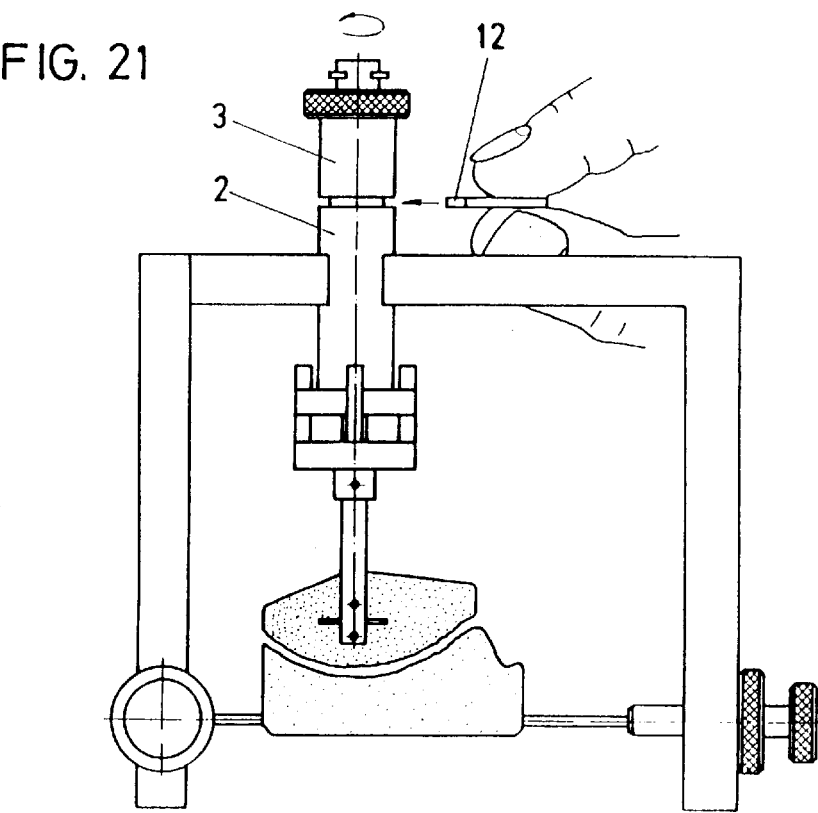
FIG. 21 shows a side elevation view of the entire apparatus of FIG. 19 after the permanent upper casting has been displaced by a uniform distance from the lower casting.

FIG. 21 shows a side elevation view of the entire apparatus of FIG. 19 after the permanent upper casting has been displaced by a uniform distance "A" from the lower casting using the measuring spacer 12, in preparation of filling the space by conventional methods with conventional materials typically used for forming protheses, including but not limited to hard wax and conventional acrylic plastics. Distance "A" is typically selected form the range of about 0.5 mm to about 3.0 mm.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. A method for forming a palatal plate prosthesis of a substantially precise, predetermined uniform thickness, comprising:

providing an apparatus for forming said palate prosthesis, which includes a frame having a first support, a second support and a third support; a first component further including elements further including a first casting support for enabling it to be detachably fixed to each of said first support, said second support and said third support, and for detachably fixing a first casting to said frame; and attached to said first support and said second support for enabling a second casting to be displaced relative to said first casting; wherein said elements are designed for causing said first casting to generally lie in a first horizontal plane when said first component is detachably fixed to said support; and, a second component attached to the upper portion of said frame generally spaced from and parallel to each said support, for movably fixing a second casting to said frame, sufficient for enabling said second casting to lie generally in a second plane which is generally parallel to, and equidistant from, said first horizontal plane when said first component is detachably fixed to said support;

providing said first casting fixed on said first component;

forming a substantially exact convex impression of said palate on a temporary elastomeric mold;

impressing said substantially exact convex impression of said palate on said temporary elastomeric mold upon said first casting sufficient to temporarily fix said temporary elastomeric mold to said first casting and provide a substantially exact concave impression of said palate on said first casting;

positioning the temporarily fixed temporary elastomeric mold and said first casting on said lower casting support;

vertically extending said second component sufficient to cause its lowest end to become temporarily fixed to said temporary elastomeric mold;

fixing said temporarily fixed temporary elastomeric mold and said first casting to said first casting support;

detaching said first casting support from said third support;

displacing said apparatus relative to said first support and said second support sufficient to cause said temporary elastomeric mold to become detached from said first casting;

removing said temporary elastomeric mold from said second component;

restoring said apparatus back to its state as characterized by said detaching;

reattaching said casting support to said third support;

forming said second casting upon said lower casting and around the lower end of said second component sufficient for impressing a substantially exact convex impression of said palate on said second casting;

manipulating said second component sufficient to cause a vertical displacement between said first impression and said second impression, substantially precisely equal to said predetermined uniform thickness; and, forming said palatal plate prosthesis within said vertical displacement.

2. The method of claim 1, wherein said vertical displacement is selected from a range of about from 0.5 to 3.0 mm.

3. The method of claim 2, wherein the material of construction of said palatal plate prosthesis is selected from the group of consisting of conventional acrylic plastics, hard wax, and combinations thereof.

4. An apparatus for forming a palatal plate prosthesis of a substantially precise, predetermined uniform thickness, comprising:

a frame including a first support, a second support and a third support;

a first component including elements for enabling it to be detachably fixed to each of said first support, said second support and said third support and for detachably fixing a first casting to said frame; and attached to said first support and said second support for enabling a second casting to be displaced relative to said first casting; wherein said elements are sufficient for causing said first casting to generally lie in a first horizontal plane when said first component is detachably fixed to said support;

wherein said first component further includes three screw threaded exposed ends; and, wherein each of said elements further includes:

a lower casting mounting element retention bolt assembly further including;
    an outer screw threaded rod member perpendicularly attached to a disk-like base and an outer knurled nut for engaging the outer screw threads of said rod member when the lower casting mounting element is fixed to said frame; wherein the end of said rod opposite the disk, further includes an axial threaded bore, for accommodating one of said screw threaded exposed ends;
a second component attached to the upper portion of said frame generally spaced from and parallel to each said support, for movably fixing a second casting to said frame, sufficient for enabling said second casting to lie generally in a second plane which is generally parallel to, and equidistant from, said first horizontal plane when said first component is detachably fixed to said support;
wherein said second component further includes:
    a shaft having at least one retention element at the lowest end thereof, for fixing said second casting thereto; and,
    a shaft elevator for vertically, non-rotationally, displacing said shaft;
a stop for stopping downward vertical travel of said shaft elevator; and,
a spacer having a thickness substantially equal to said substantially precise, predetermined uniform thickness, insertable between the lowest outermost end of said shaft elevator and said stop.

5. An apparatus for forming a palatal plate prosthesis of a substantially precise, predetermined uniform thickness, comprising:
    a frame including a first support, a second support and a third support;
    a first component further including elements for enabling it to be detachably fixed to each of said first support, said second support and said third support, for detachably fixing a first casting to said frame; and attached to said first support and said second support for enabling a second casting to be displaced relative to said first casting; wherein said elements are designed for causing said first casting to generally lie in a first horizontal plane when said first component is detachably fixed to said support; and,
    a second component attached to the upper portion of said frame generally spaced from and parallel to each said support, for movably fixing a second casting to said frame, sufficient for enabling said second casting to lie generally in a second plane which is generally parallel to, and equidistant from, said first horizontal plane when said first component is detachably fixed to said support.

6. The apparatus of claim 5, wherein said frame further includes a first support, a second support and a third support.

7. The apparatus of claim of claim 6, wherein said first component further includes three screw threaded exposed ends.

8. The apparatus of claim 7, wherein each of said elements includes a lower casting mounting element retention bolt assembly comprising: an outer screw threaded rod member perpendicularly attached to a disk-like base and an outer knurled nut for engaging the outer screw threads of said rod member when the lower casting mounting element is fixed in frame; wherein the end of said rod opposite the disk, further includes an axial threaded bore, for accommodate one of said screw threaded exposed ends.

9. The apparatus of claim 6, wherein said second component further includes: a shaft having at least one retention element at the lowest end thereof, for fixing said second casting thereto; and, a shaft elevator for vertically, non-rotationally, displacing said shaft.

10. The apparatus of claim 9, wherein said second component further includes: a stop positioned between said shaft elevator and said fourth component for stopping downward vertical travel of said shaft elevator.

11. The apparatus of claim 10, further including a spacer having a thickness substantially equal to said substantially precise, predetermined uniform thickness, insertable between the lowest most end of said shaft elevator and said stop.

* * * * *